United States Patent
Fu et al.

(10) Patent No.: US 11,141,458 B2
(45) Date of Patent: Oct. 12, 2021

(54) COMPOSITION AND METHODS FOR PROMOTING AND TREATING CHRONIC WOUND HEALING

(71) Applicant: MYCOMAGIC BIOTECHNOLOGY CO., LTD, New Taipei (TW)

(72) Inventors: Hsu-Yuan Fu, New Taipei (TW); Yu-Che Cheng, Taipei (TW)

(73) Assignee: MYCOMAGIC BIOTECHNOLOGY CO., LTD., New Taipei (TW)

( * ) Notice: Subject to any disclaimer, the term of this patent is extended or adjusted under 35 U.S.C. 154(b) by 0 days.

(21) Appl. No.: 16/514,740

(22) Filed: Jul. 17, 2019

(65) Prior Publication Data

US 2021/0015890 A1 Jan. 21, 2021

(51) Int. Cl.
| | | |
|---|---|---|
| *A61K 38/16* | (2006.01) | |
| *A61K 38/08* | (2019.01) | |
| *A61K 47/46* | (2006.01) | |
| *A61K 47/38* | (2006.01) | |
| *A61K 9/06* | (2006.01) | |
| *A61P 17/02* | (2006.01) | |
| *A61K 47/32* | (2006.01) | |
| *A61K 45/06* | (2006.01) | |
| *A61K 9/00* | (2006.01) | |

(52) U.S. Cl.
CPC ............... *A61K 38/16* (2013.01); *A61K 9/06* (2013.01); *A61K 38/08* (2013.01); *A61K 47/32* (2013.01); *A61K 47/38* (2013.01); *A61K 47/46* (2013.01); *A61P 17/02* (2018.01); *A61K 9/0014* (2013.01); *A61K 45/06* (2013.01)

(58) Field of Classification Search
CPC .......... A61K 38/16; A61K 9/06; A61K 38/08; A61K 47/32; A61K 47/38; A61K 47/46; A61K 9/0014; A61K 45/06; A61P 17/02
See application file for complete search history.

(56) References Cited

U.S. PATENT DOCUMENTS

| | | | | |
|---|---|---|---|---|
| 5,271,943 A | * | 12/1993 | Bogart | ............... A61L 26/0014 424/484 |
| 7,601,808 B2 | * | 10/2009 | Lin | ...................... C07K 14/375 530/350 |
| 9,623,074 B2 | * | 4/2017 | Ou | ......................... A61P 17/02 |
| 2014/0079737 A1 | | 3/2014 | Ou et al. | |

FOREIGN PATENT DOCUMENTS

TW    201410253 A    3/2014

OTHER PUBLICATIONS

"Material Safety Data Sheet Phosphate Buffered Saline Solution 10X". 2009. Scholar Chemistry. MSDS # 533.10, p. 1-2 (Year: 2009).*
Khan, AW et al. "Formulation development, optimization and evaluation of aloe vera gel for wound healing". Oct.-Dec. 2013, Pharmacognosy Magazine, 9(Suppl 1): S6-S10 (Year: 2013).*
Landis, SJ. "Chronic Wound Infection and Antimicrobial Use". Nov. 2008. Advances in Skin & Wound Care, vol. 21, Issue 11, p. 531-540. (Year: 2008).*
"Regranex Gel". McNeill Pharmaceutical, 1998. (Year: 1998).*
Office Action and Search Report dated Oct. 29, 2020 issued by Taiwan Intellectual Property Office for corresponding Taiwan, R.O.C. Patent application No. 108134003.
English Summary of Office Action dated Oct. 29, 2020 issued by Taiwan Intellectual Property Office for corresponding Taiwan, R.O.C. Patent application No. 108134003.
English Translation of Search Report dated Oct. 29, 2020 issued by Taiwan Intellectual Property Office for corresponding Taiwan, R.O.C. Patent application No. 108134003.
TW201410253A Corresponds to US20140079737A1.

* cited by examiner

*Primary Examiner* — Ruixiang Li
(74) *Attorney, Agent, or Firm* — WPAT, P.C.; Anthony King

(57) ABSTRACT

The present disclosure provides compositions comprising *Ganoderma* immunomodulatory protein or a recombinant thereof and a gel-forming agent. Also provided are methods for the treatment of chronic wounds, ulcers or sores, and methods using the compositions.

11 Claims, 5 Drawing Sheets

Specification includes a Sequence Listing.

(A)

(B)

(C)

(A) (B)

(C) (D)

(A)

(B)

(A)

(B)

(A)

(B)

(C)

(D)

COMPOSITION AND METHODS FOR PROMOTING AND TREATING CHRONIC WOUND HEALING

FIELD OF THE INVENTION

The present disclosure relates to a composition and method for promoting chronic wound healing or treating ulcers. Particularly, the present disclosure provides an immunomodulatory protein composition and its applications in enhancing chronic wound healing and treating ulcers.

BACKGROUND OF THE INVENTION

Wound healing is a complex dynamic process that results in the restoration of anatomic continuity and function. The typical model of wound healing is divided into three sequential, yet overlapping phases, namely: inflammatory, proliferative and finally remodeling.

For people with diabetes, injuries such as minor wounds, cuts, and burns can lead to serious health issues. Many people with diabetes develop wounds that are slow to heal, do not heal well, or never heal. Sometimes, an infection might develop. High levels of blood glucose caused by diabetes can, over time, affect the nerves (neuropathy) and lead to poor blood circulation, making it hard for blood—needed for skin repair—to reach areas of the body affected by sores or wounds. If an infection develops in the wound and is left untreated, it can progress to the stage of gangrene. Most chronic wounds are ulcers that are associated with ischemia, diabetes mellitus, venous stasis or pressure. The prevalence is expected to increase as the population ages and the number of individuals with diabetes mellitus increases. Chronic ulcers reduce the quality of life and working capacity of the patient, and represent a substantial financial burden to the health care system. Sometimes, people with uncontrolled infections develop sepsis, which occurs when an infection spreads into the bloodstream. Sepsis can be life-threatening.

US 20130172256 discloses a method of treating diabetes-related impaired wound healing, which includes the step of administering an effective amount of estrogen replacement therapy to a patient in need thereof to promote wound healing. U.S. Pat. No. 9,623,074B2 discloses providing a method for promoting wound healing or tissue injury treatment in a subject in need thereof, the method comprising administering to the subject an effective amount of one or more fungal immunomodulatory protein (preferably, Ganoderma immunomodulatory protein). US 20170014484 provides a method of treating a wound in a diabetic patient including administering a therapeutically effective amount of Chemokine (C-C motif) ligand 2 (CCL2) to a wound site.

However, although there have been extensive drugs or compositions developed for wound healing treatment, the healing of chronic wounds and ulcers is still a complex task.

SUMMARY OF THE INVENTION

The present disclosure surprisingly found that Ganoderma immunomodulatory protein or a recombinant thereof provides advantageous efficacy in treating, alleviating, promoting or accelerating the healing of a chronic wound, ulcer or sore. Accordingly, the present disclosure provides a composition and method in treating, alleviating, promoting or accelerating the healing of a chronic wound, ulcer or sore.

In one aspect, the present disclosure provides a composition comprising a gel-forming agent in an amount from about 0.1% (w/w) to about 2% (w/w) and an immunomodulatory protein in an amount from about 0.0001% (w/w) to about 0.05% (w/w), wherein the immunomodulatory protein comprises an amino acid sequence selected from the group consisting of SEQ ID NO: 1 to 4.

The sequences of SEQ ID NO: 1 to 4 are listed as follows.

(SEQ ID NO: 1)
LAWNVK (SEQ ID NO: 2)
DLGVRPSYAV (SEQ ID NO: 3)
MSDTALIFTLAWNVKQLAFDYTPNWGRGRPSSFIDTVTFPTVLTDKAYTY
RVVVSGKDLGVRPSYAVESDGSQKINFLEYNSGYGIADTNTIQVYVIDPD
TGNNFIVAQWN (SEQ ID NO: 4)
EAEAEFMSDTALIFTLAWNVKQLAFDYTPNWGRGRPSSFIDTVTFPTVLT
DKAYTYRVVVSGKDLGVRPSYAVESDGSQKINFLEYNSGYGIADTNTIQV
YVIDPDTGNNFIVAQWNYLEQKLISEEDLNSAVDHHHHHH

Examples of gel-forming agent include, but are not limited to, polyethylene glycol (PEG)-diacrylate, PEG-acrylate, PEG-thiol, PEG-azide, PEG-alkyne, chitosan, hyaluronic acid, collagen, fibrin, acacia, alginic acid, natto gum, aloe vera, bentonite, carbomers, carboxymethyl cellulose, ethylcellulose, gelatin, elastin, hydroxypolyamide, hydroxyethyl cellulose, hydroxypropyl cellulose, hydroxypropyl methylcellulose, magnesium aluminum silicate, methylcellulose, poloxamers, polyvinyl alcohol, sodium alginate, tragacanth, xanthan gum, gelatin, carboxyvinyl polymers, starch, water-swellable hydrocolloids, carragenans, hyaluronates, agarose, alginates, acrylates and ammonium acryloyldimethyltaurate/VP copolymer.

In some embodiments, the gel-forming agent is xanthan gum, methylcellulose, or ammonium acryloyldimethyltaurate/VP copolymer.

In one embodiment, the composition has a pH ranging from about 5.5 to about 7.5. In some embodiments, the pH ranges from about 6.0 to about 7.5, about 6.5 to about 7.5, about 5.5 to about 7.0, about 6.0 to about 7.0, about 6.5 to about 7.0, about 5.5 to about 6.5, or about 6.0 to about 6.5.

In one embodiment, the composition has a viscosity ranging from about 0.05 Pa·s to about 200 Pa·s. In some embodiments, the viscosity ranges from about 0.1 Pa·s to about 200 Pa·s, about 0.5 Pa·s to about 200 Pa·s, about 1.0 Pa·s to about 200 Pa·s, about 5 Pa·s to about 200 Pa·s, about 10.0 Pa·s to about 200 Pa·s, about 20.0 Pa·s to about 200 Pa·s, about 40.0 Pa·s to about 200 Pa·s, about 60.0 Pa·s to about 200 Pa·s, about 80.0 Pa·s to about 200 Pa·s, about 100.0 Pa·s to about 200 Pa·s, about 120 Pa·s to about 200 Pa·s, about 140 Pa·s to about 200 Pa·s, about 160 Pa·s to about 200 Pa·s, about 0.05 Pa·s to about 160 Pa·s, 0.05 Pa·s to about 140 Pa·s, 0.05 Pa·s to about 120 Pa·s, 0.05 Pa·s to about 100 Pa·s, 0.05 Pa·s to about 80 Pa·s, 0.05 Pa·s to about 60 Pa·s, 0.05 Pa·s to about 40 Pa·s, 0.05 Pa·s to about 20 Pa·s, 0.05 Pa·s to about 10 Pa·s, 0.05 Pa·s to about 5.0 Pa·s, 0.05 Pa·s to about 3.0 Pa·s or 0.05 Pa·s to about 1.0 Pa·s.

In some embodiments, the amount of the immunomodulatory protein ranges from about 0.0001% (w/w) to about 0.03% (w/w), about 0.0001% (w/w) to about 0.01% (w/w), about 0.0001% (w/w) to about 0.03% (w/w), about 0.0001% (w/w) to about 0.01% (w/w), about 0.0001% (w/w) to about 0.005% (w/w), about 0.0001% (w/w) to about 0.003% (w/w), about 0.0001% (w/w) to about 0.001% (w/w) or about 0.0001% (w/w) to about 0.0005% (w/w).

In some embodiments, the amount of the gel-forming agent ranges from about 0.5% (w/w) to about 2.0% (w/w), about 0.5 (w/w) to about 1.5% (w/w), about 0.5 (w/w) to about 1.2% (w/w), about 0.5 (w/w) to about 1.0% (w/w), about 0.1 (w/w) to about 1.5% (w/w), about 0.1 (w/w) to about 1.0% (w/w), about 0.1 (w/w) to about 0.5% (w/w), about 1.0% (w/w) to about 2.0% (w/w), or about 1.5% (w/w) to about 2% (w/w).

In another aspect, the present disclosure provides a method for treating, alleviating, accelerating or promoting the healing of a chronic wound, ulcer or sore, comprising providing an effective amount of the pharmaceutical composition described herein to a subject in need thereof.

In one embodiment, the effective amount of the immunomodulatory protein ranges from about 1 mcg/cm$^2$ to about 100 mcg/cm$^2$, about 1 mcg/cm$^2$ to about 80 mcg/cm$^2$, about 1 mcg/cm$^2$ to about 60 mcg/cm$^2$, about 1 mcg/cm$^2$ to about 40 mcg/cm$^2$, about 1 mcg/cm$^2$ to about 20 mcg/cm$^2$, about 1 mcg/cm$^2$ to about 10 mcg/cm$^2$, about 1 mcg/cm$^2$ to about 5 mcg/cm$^2$, about 5 mcg/cm$^2$ to about 100 mcg/cm$^2$, about 10 mcg/cm$^2$ to about 100 mcg/cm$^2$, about 20 mcg/cm$^2$ to about 100 mcg/cm$^2$, about 40 mcg/cm$^2$ to about 100 mcg/cm$^2$, about 60 mcg/cm$^2$ to about 100 mcg/cm$^2$ or about 80 mcg/cm$^2$ to about 100 mcg/cm$^2$.

In one embodiment, the chronic wound, ulcer or sore is associated with diabetes mellitus.

In one embodiment, the chronic wound, ulcer or sore is associated with decreased circulation of blood, a venous leg ulcer, a venous foot ulcer, an arterial leg ulcer, an arterial foot ulcer, or a decubitus ulcer.

In one embodiment, the method further comprises administering one or more additional antibiotic or antimicrobial agents to the subject.

DETAILED DESCRIPTION OF THE INVENTION

Figure 1:
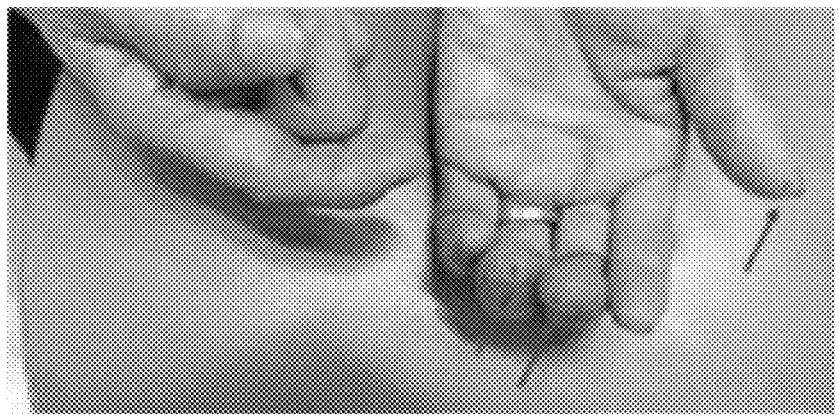
FIG. 1 shows the treatment of a chronic wound with the hydrogel of the present disclosure ((A) before treatment; (B) and (C) after treatment for one week and for two weeks, respectively).
Figure 1:
Figure 1:
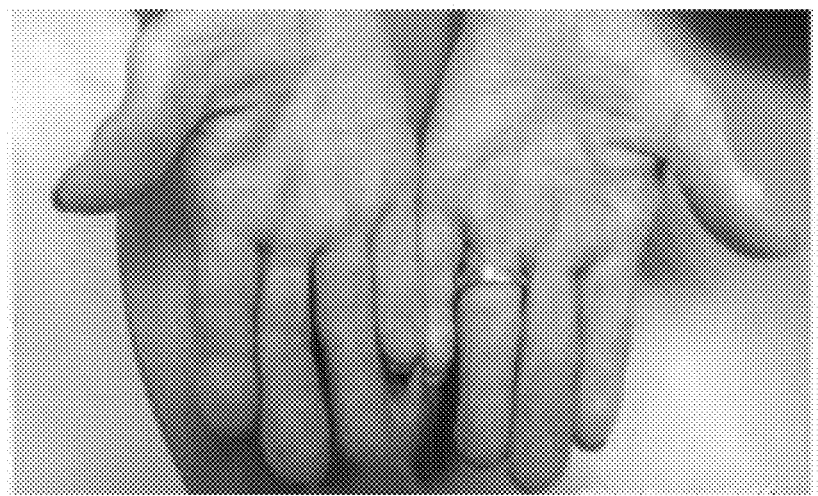
Figure 2:
FIG. 2 shows the treatment of diabetic bed sores with the hydrogel of the present disclosure ((A) before treatment; (B), (C) and (D) after treatment with 6, 8 and 14 days, respectively).
Figure 2:
Figure 2:
Figure 2:

Unless defined otherwise, all technical and scientific terms used herein have the same meaning as commonly understood by one of ordinary skill in the art to which this invention belongs. Although any methods and materials similar or equivalent to those described herein can be used in the practice or testing of the invention, the preferred methods and materials are now described. All publications mentioned herein are incorporated herein for reference.

In this application, the use of the singular includes the plural, the article "a" or "an" meaning "at least one", and the use of "or" means "and/or", unless specifically stated otherwise.

The term "topical" refers to administration or delivery of a compound by application of the compound to a surface of a body part.

The term "wound healing" refers to the restoration of the tissue integrity, either in part or in full.

As used herein, the term "chronic wound" refers to a wound that has not healed within a normal time period for healing in an otherwise healthy subject. Chronic wounds may be those that do not heal because of the health of the subject; for example, where the subject has poor circulation or a disease such as diabetes, or where the subject is on a medication that inhibits the normal healing process. In some instances a chronic wound may remain unhealed for weeks, months or even years. Examples of chronic wounds include but are not limited to, diabetic ulcers, pressure sores and tropical ulcers.

As used herein, "promote" or "increase," or "promoting" or "increasing" are used interchangeably herein. These terms refer to the increase in a measured parameter in a treated cell, tissue or subject in comparison to an untreated cell, tissue or subject. A comparison can also be made of the same cell or tissue or subject before and after treatment. In some embodiments, the increase in the treated cell, or tissue or subject is at least about 10%, 20%, 30%, 40%, 50%, 60%, 70%, 80%, 90%, 1-fold, 2-fold, 3-fold, 4-fold or more in comparison to an untreated cell, or tissue or subject.

As used herein, "treatment," "treating" or "ameliorating" are used interchangeably. These terms refer to an approach for obtaining beneficial or desired results including, but not limited to, therapeutic benefit and/or a prophylactic benefit.

The term "promoting wound healing" as used herein, refers to improving wound healing compared to the wound healing that would be observed in an untreated wound.

As used herein, "effective amount" means an amount sufficient to treat a subject afflicted with a disease or to alleviate a symptom or a complication associated with the disease.

As used herein, "subject" refers to either a human or non-human animal.

As used herein, the term "topical formulation" (synonymously, "topical composition") is used herein to refer to a pharmaceutical preparation intended for topical or local application to an afflicted region of a subject in need thereof.

The present disclosure provides compositions comprising Ganoderma immunomodulatory protein or a recombinant thereof and a gel-forming agent. The present disclosure provides methods for the treatment of chronic wounds, ulcers or sores, and methods using the compositions. The compositions are intended to be topically applied in various ways which will be further described.

The *Ganoderma* immunomodulatory protein or a recombinant thereof comprises an amino acid sequence selected from the group consisting of SEQ ID NO: 1 to 4. The preparation of the *Ganoderma* immunomodulatory protein or a recombinant thereof has been described in U.S. Pat. No. 7,601,808. The Ganoderma immunomodulatory protein or a recombinant thereof is in an amount from about 0.0001% (w/w) to about 0.05% (w/w).

The composition of the present disclosure also comprises a gel-forming agent to form a topical gel product with a viscosity ranging from about about 0.05 Pa·s to about 200 Pa·s.

The composition of the present disclosure is formulated as having a pH from 5.5 to 7.5. In one embodiment, the pH of the aqueous medium can be adjusted by means of low concentrations of suitable biocompatible buffering ingredients, non-limiting examples being tromethamine, sodium carbonate and bicarbonate, as well as sodium dihydrogen phosphate and disodium hydrogen phosphate.

A composition of the present disclosure may also contain one or more additional antimicrobial agents to potentiate its bactericidal action on important pathogens such as *Staphylococcus aureus* or *Pseudomonas aeruginosa*, prevent the overgrowth of any strains that develop resistance during prolonged treatment, or broaden the antimicrobial spectrum to include non-bacterial pathogens, including but not limited to fungi.

The dosage of the immunomodulatory protein, recombination thereof or composition suitable for use according to the present invention can be determined by those skilled in the art on the basis of the disclosure herein. The medicament will contain an effective dosage (depending upon the route of administration and pharmacokinetics of the active agent) of suitable pharmaceutical carriers and excipients suitable for the topical route of administration of the formulation.

In one embodiment, a dosage regimen is repeated, such as once, two times, three times or more; for example repeated for the rest of the lifespan of a subject in need. In another embodiment, patients are treated with a dosage regime of 14 days treatment with pharmaceutical composition according to the present disclosure.

The present invention provides pharmaceutical compositions and methods for treatment of chronic wounds, ulcers or sores of the skin, and mucosal membranes or connective tissue of the body, which may be chronic. The chronic wounds, ulcers or sores may be caused by a broad spectrum of events and/or may be associated with other diseases. Chronic wounds, now generally called "non-healing wounds", or lesions, wounds or ulcers arise when a wound fails to follow an appropriate timely healing process to achieve the normal sustained and stable anatomic and functional integrity of the healed tissue. A skin lesion which has failed to make substantial progress towards healing within a period of three months, or which has become stable in a partially healed state for more than three months, could be categorized as a chronic or "non-healing" wound. As the age and fitness of the patient, as well as other factors such as diseases or disorders suffered by the patient (for example, circulatory disorders), can significantly lengthen the normal healing process. In such circumstances a skin lesion which is unhealed after six months can be categorized as a "non-healing" wound. A "non-healing" wound or chronic skin lesion is ulcerous when it involves focal loss of epidermis and at least part of the dermis. Chronic ulcerous skin lesions are usually accompanied by other symptoms apart from the failure of the normal healing process. Typical accompanying signs and symptoms include one or more of the following: pain, exudation, bad smell, excoriation, wound spreading, tissue necrosis, irritational thinking, and hyperkeratosis.

In some embodiments, the chronic wounds, ulcers or sores to be treated include those associated with decreased circulation of blood, such as leg ulcers and foot ulcers associated with venous insufficiency or arterial insufficiency, decubitus ulcers, pressure sores or bedsores, and lesions associated with diabetes mellitus.

The following examples are offered to illustrate, but not limit the claimed invention.

EXAMPLES

Example 1 Preparation of Hydrogel of the Present Disclosure

The embodiments of the formulations of the hydrogels are listed in below table.

| No. | Gel-forming agent | Immunomodulatory protein | Ultrapure water | pH |
|---|---|---|---|---|
| A | 0.8% (w/w) ammonium acryloyldimethyltaurate/ VP copolymer | 0.005% (w/w) | Balance | ~6.5 |
| B | 2% (w/w) aloe vera | 0.05% (w/w) | Balance | ~6 |
| C | 0.1% (w/w) methylcellulose | 0.0001% (w/w) | Balance | ~6.5 |
| D | 0.5% (w/w) xanthan gum | 0.001% (w/w) | Balance | ~7 |
| E | 1% (w/w) sodium alginate | 0.01% (w/w) | Balance | ~5.5 |

The the immunomodulatory proteins with SEQ ID NO:4 were added to ultrapure water and then well-mixed. Subsequently, the gel-forming agent was added to the resulting mixture by continuous stirring until the gels were formed. The resulting gels were incubated a refrigerator at 4° C. for at least 16 hours. The resulting gels were placed in an appropriate contain for storage.

Example 2 Treatment of Chronic Wounds

A patient suffered from chronic wounds in the fingertips for more than two years and the lesions could not heal. After applying the hydrogel C of Example 1 to the wounds for one or two weeks, the chronic wounds were healed (FIGS. 1(A) to (C)).

Example 3 Treatment of Wound, Ulcer or Sores Associated with Diabetes Mellitus

In the first case report, a patient suffered from bed sores associated with diabetes mellitus (DM) for one month and the lesions could not heal. After applying the hydrogel B of Example 1 to the sore for 6 days, 8 days and two weeks, the sores were reduced and the lesions were healed (FIGS. 2(A) to (D)).

Figure 3:
FIG. 3 shows the treatment of a diabetic foot with the hydrogel of the present disclosure ((A) before treatment; (B) after treatment with 82 days).
Figure 3:

In the second case report, a 89-year old, female DM patient suffered from diabetic foot and was then subjected to amputation. After the surgical operation, the wound could not be healed and thus suffered from infection. After applying the hydrogel A of Example 1 to the wound for 82 days, the wound healed (FIGS. 3(A) and (B)).

Figure 4:
FIG. 4 shows the treatment of a chronic bed sore with the hydrogel of the present disclosure ((A) before treatment; and (B) after treatment for 3 days).
Figure 4:

In the third case report, a DM patient suffered from plantar chronic ulceration for three months. After applying the hydrogel E of Example 1 to the ulcer for 17 days, the ulcer reduced and the lesions were healed (FIGS. 4(A) and (B)).

Example 4 Treatment of Venous Ulcer

Figure 5:
FIG. 5 shows the treatment of a onycholysis ulcer with the hydrogel of the present disclosure ((A) before treatment; (B), (C), and (D) after treatment with 1, 4 and 7 days)).
Figure 5:
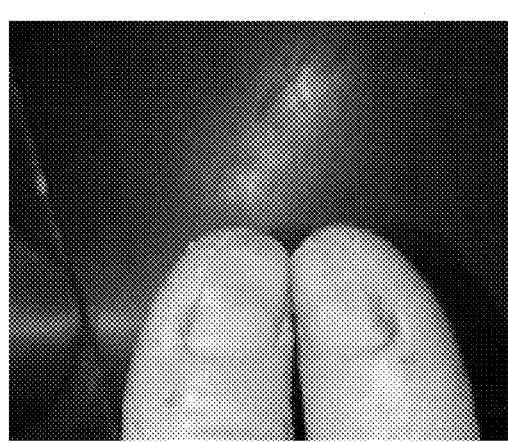
Figure 5:
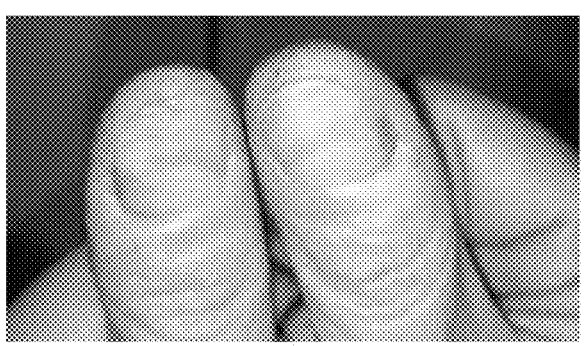
Figure 5:
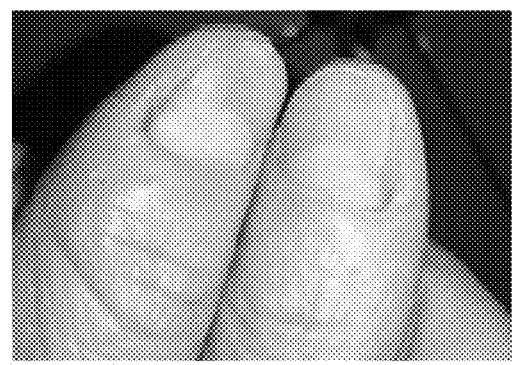

In a case report, a systemic lupus erythematosus patient suffered from a static ulcer. After applying the hydrogel D of Example 1 to the ulcer for 14 days, the ulcer was reduced and the lesions were healed (FIGS. 5(A) and (B)).

What is claimed is:

1. A composition comprising a gel-forming agent in an amount from 0.1% (w/w) to 2% (w/w) and an immunomodulatory protein in an amount from 0.0001% (w/w) to 0.05% (w/w), wherein the immunomodulatory protein comprises an amino acid sequence selected from the group consisting of SEQ ID NO: 1 to 4; and wherein the composition has a pH ranging from 5.5 to 7.

2. The composition of claim 1, wherein the immunomodulatory protein comprises an amino acid sequence consisting of SEQ ID NO:4.

3. The composition of claim 1, wherein the gel-forming agent is polyethylene glycol (PEG)-diacrylate, PEG-acrylate, PEG-thiol, PEG-azide, PEG-alkyne, chitosan, hyaluronic acid, collagen, fibrin, acacia, alginic acid, natto gum, aloe vera, bentonite, carbomers, carboxymethyl cellulose, ethylcellulose, gelatin, elastin, hydroxypolyamide, hydroxyethyl cellulose, hydroxypropyl cellulose, hydroxypropyl methylcellulose, magnesium aluminum silicate, methylcellulose, poloxamers, polyvinyl alcohol, sodium alginate, tragacanth, xanthan gum, gelatin, carboxyvinyl polymers, starch, water-swellable hydrocolloids, carrageenans, hyaluronates, agarose, alginates, acrylates or ammonium acryloyldimethyltaurate/VP copolymer or a combination thereof.

4. The composition of claim 1, wherein the gel-forming agent is xanthan gum, methylcellulose, natto gum, aloe vera, or ammonium acryloyldimethyltaurate/VP copolymer.

5. The composition of claim 1, wherein the composition has a viscosity ranging from 0.05 Pa·s to 200 Pa·s.

6. The composition of claim 1, wherein the amount of the gel-forming agent ranges from 0.5 (w/w) to 1.2% (w/w).

7. A method for treating, alleviating, accelerating or promoting the healing of a chronic wound, ulcer or sore, comprising providing an effective amount of the pharmaceutical composition of claim 1 to a subject in need thereof.

8. The method of claim 7, wherein the chronic wound, ulcer or sore is associated with decreased circulation of blood, a venous leg ulcer, a venous foot ulcer, an arterial leg ulcer, an arterial foot ulcer, or a decubitus ulcer.

9. The method of claim 7, wherein the chronic wound, ulcer or sore is associated with diabetes mellitus.

10. The method of claim 7, wherein the effective amount of the immunomodulatory protein ranges from 1 mcg/cm$^2$ to 100 mcg/cm$^2$.

11. The method of claim 7, wherein the method further comprises administering one or more additional antibiotic or antimicrobial agents to the subject.

\* \* \* \* \*

SEQUENCE LISTING

<160> NUMBER OF SEQ ID NOS: 4

<210> SEQ ID NO 1
<211> LENGTH: 6
<212> TYPE: PRT
<213> ORGANISM: Ganoderma microsporum

<400> SEQUENCE: 1

Leu Ala Trp Asn Val Lys
1               5

<210> SEQ ID NO 2
<211> LENGTH: 10
<212> TYPE: PRT
<213> ORGANISM: Ganoderma microsporum

<400> SEQUENCE: 2

Asp Leu Gly Val Arg Pro Ser Tyr Ala Val
1               5                   10

<210> SEQ ID NO 3
<211> LENGTH: 111
<212> TYPE: PRT
<213> ORGANISM: Ganoderma microsporum

<400> SEQUENCE: 3

Met Ser Asp Thr Ala Leu Ile Phe Thr Leu Ala Trp Asn Val Lys Gln
1               5                   10                  15

Leu Ala Phe Asp Tyr Thr Pro Asn Trp Gly Arg Gly Arg Pro Ser Ser
            20                  25                  30

Phe Ile Asp Thr Val Thr Phe Pro Thr Val Leu Thr Asp Lys Ala Tyr
        35                  40                  45

Thr Tyr Arg Val Val Ser Gly Lys Asp Leu Gly Val Arg Pro Ser
    50                  55                  60

Tyr Ala Val Glu Ser Asp Gly Ser Gln Lys Ile Asn Phe Leu Glu Tyr
65                  70                  75                  80

Asn Ser Gly Tyr Gly Ile Ala Asp Thr Asn Thr Ile Gln Val Tyr Val
                85                  90                  95

Ile Asp Pro Asp Thr Gly Asn Asn Phe Ile Val Ala Gln Trp Asn
            100                 105                 110

<210> SEQ ID NO 4
<211> LENGTH: 140
<212> TYPE: PRT
<213> ORGANISM: Ganoderma microsporum

<400> SEQUENCE: 4

Glu Ala Glu Ala Glu Phe Met Ser Asp Thr Ala Leu Ile Phe Thr Leu
1               5                   10                  15

Ala Trp Asn Val Lys Gln Leu Ala Phe Asp Tyr Thr Pro Asn Trp Gly
            20                  25                  30

Arg Gly Arg Pro Ser Ser Phe Ile Asp Thr Val Thr Phe Pro Thr Val
        35                  40                  45

Leu Thr Asp Lys Ala Tyr Thr Tyr Arg Val Val Ser Gly Lys Asp
    50                  55                  60

Leu Gly Val Arg Pro Ser Tyr Ala Val Glu Ser Asp Gly Ser Gln Lys
65                  70                  75                  80

Ile Asn Phe Leu Glu Tyr Asn Ser Gly Tyr Gly Ile Ala Asp Thr Asn
                85                  90                  95

-continued

```
Thr Ile Gln Val Tyr Val Ile Asp Pro Asp Thr Gly Asn Asn Phe Ile
            100                 105                 110

Val Ala Gln Trp Asn Tyr Leu Glu Gln Lys Leu Ile Ser Glu Glu Asp
        115                 120                 125

Leu Asn Ser Ala Val Asp His His His His His
        130                 135             140
```